United States Patent [19]
Hallett et al.

[11] Patent Number: 5,719,397
[45] Date of Patent: Feb. 17, 1998

[54] TARGET MATERIAL DETECTION

[75] Inventors: William A. Hallett, London; Joshua D. Silver, Oxford, both of England

[73] Assignee: Spectrasense Limited, Oxford, United Kingdom

[21] Appl. No.: 624,487

[22] PCT Filed: Oct. 4, 1994

[86] PCT No.: PCT/GB94/02155
§ 371 Date: Apr. 4, 1996
§ 102(e) Date: Apr. 4, 1996

[87] PCT Pub. No.: WO95/10037
PCT Pub. Date: Apr. 13, 1995

[30] Foreign Application Priority Data

Oct. 4, 1993 [GB] United Kingdom ............ 9320416
Oct. 15, 1993 [GB] United Kingdom ............ 9321275

[51] Int. Cl.$^6$ ............................................. G01M 21/59
[52] U.S. Cl. ........................................... 250/339.13
[58] Field of Search ................. 250/339.13, 338.5, 250/343

[56] References Cited

U.S. PATENT DOCUMENTS

| | | |
|---|---|---|
| 3,069,247 | 12/1962 | Barry . |
| 3,893,770 | 7/1975 | Takami et al. ............ 250/345 |
| 5,013,153 | 5/1991 | Disch et al. ............ 356/346 |
| 5,017,785 | 5/1991 | Räsänen ............ 250/347 |
| 5,223,715 | 6/1993 | Taylor ............ 250/343 |

FOREIGN PATENT DOCUMENTS

| | | |
|---|---|---|
| 0354298 | 4/1989 | European Pat. Off. . |
| 0382908 | 11/1989 | European Pat. Off. . |
| 2344398 | 9/1973 | Germany . |

OTHER PUBLICATIONS

Automatisierungstechnishe Praxis ATP, vol. 32, No. 7, Jul. 1990, Munchen DE, pp. 338–342, "Entwicklungstendenzen der Betriebsanalysentechnik", see p. 341, right col.; figure 6.

Technisches Messen Tm, vol. 52, No. 6, Jun. 1985, Munchen DE, pp. 242–246, G. Schmidtke et al. "Spectroskopische Umweltme technik", see p. 243, left col.; figure 2.

IEEE Transactions on Industry Applications, vol. 29, No. 4, Jul. 1993, New York, US, pp. 749–753, Dubaniewicz et al. "Fiber Optics for Atmospheric Mine Monitoring" see p. 750; figures 1,2.

Measurement Science and Technology, vol. 3, No. 2, Feb. 1992, Bristol GB, pp. 191–195, S.F. Johnston "Gas Monitors Employing Infrared LEDs", see figures 4,5.

*Primary Examiner*—Carolyn E. Fields
*Attorney, Agent, or Firm*—Watson Cole Stevens Davis, P.L.L.C.

[57] ABSTRACT

An apparatus for detecting the presence of a target material such as a multicomponent gas is disclosed. The apparatus includes a source of electromagnetic radiation and a device for dispersing the radiation into different frequency bands for targeting the material at different wavelengths corresponding to absorption bands in the material. Spaced apart optoelectric transducers detect the different frequency bands. A processor detects the changes in the output of the transducers occasioned by partial absorption of the electromagnetic radiation from the source by the target material. Processing means also compensates for temperature variations in the source.

14 Claims, 5 Drawing Sheets

TARGET MATERIAL DETECTION

TECHNICAL FIELD

This invention relates to an improved method and device for detecting the presence of a target material, e.g. gas, in a fluent composition typically comprising a mixture of gases. The invention is expected to have particular relevance to a monitor for carbon monoxide but the principles to be described will readily be seen to be usable with a wide range of target gases or even for the detection of smoke.

BACKGROUND ART

There is currently a need for a low-cost carbon monoxide detector which may be used in the home, motor car and/or work environments. In U.S. Pat. No. 5,070,244 there is disclosed a method of and apparatus for detecting the presence of a gas within an atmosphere containing the gas. The invention has particular application in the detection of a combustible gas in air but discloses broader applications for the detection of the presence of any gas, e.g. an explosive or toxic gas, in an atmosphere containing the gas. This known invention involves beaming infra-red radiation e.g. from a conventional incandescent lamp, through a chamber containing the atmosphere and detecting, e.g. in a pyroelectric dectector, the level of radiation that impinges on an infra-red detector within the chamber.

An aim of the present is to provide an improved method of detecting a substance in fluent material, preferably comprising a mixture of gases, which makes use of established low-cost electronic and optical components.

DISCLOSURE OF THE INVENTION

According to one aspect of the present invention apparatus for detecting the presence of a target material, e.g. gas, in a fluent composition, preferably comprising a mixture of gases, comprising a source of electromagnetic radiation, detector means for detecting said electromagnetic radiation from said source after passage through said fluent composition and processing means for detecting changes in the output of said detector means occasioned by partial absorption of the electromagnetic radiation from said source by the target material, is characterised in that the detector means comprises at least two spaced apart opto-electric transducers for respectively detecting selected frequency bands for which the target material has different specific absorbtivities, and in that the apparatus further comprises dispersive means for presenting the electromagnetic radiation at each of said different frequency bands to a respective one of said opto-electric transducers.

Apparatus in accordance with this invention works by detecting a relative change in electromagnetic radiation emitted by the source due to absorption of that radiation by the target material or gas. In the case of a carbon monoxide detector infra-red radiation is employed since carbon monoxide absorbs strongly between 4.5 and 5 microns. The presence of a strong absorption band at this frequency can be used as a reliable signature for the presence of CO. Carbon dioxide also has an absorption band between 4 and 4.5 microns and a carbon monoxide detector must be able to discriminate between the two. Other exotic and poisonous gases also have absorption bands in this range and the principle described here can also be extended to other gases (e.g. NO). The apparatus can also be used as a smoke detector, e.g. for detecting the presence or otherwise of smoke by itself, or the detection simultaneously of the presence of smoke and one or more other gaseous means, in a mixture of gases, e.g. the atmosphere. The apparatus could possibly also be used for detection of a target material in a liquid medium (the fluent composition).

According to another aspect of the present invention a method of detecting the presence of a target material (e.g. a target gas) in a fluent composition (preferably comprising a mixture of gases, e.g. the atmosphere) comprising detecting in detector means electromagnetic radiation emitted from a source after it has passed through said fluent composition, is characterised in that the emitted electromagnetic radiation is dispersed prior to the detector means into bands of different frequencies for which the target material has different specific absorbtivities and in that the different frequency bands are detected by spaced apart opto-electric transducers comprising said detector means.

Conveniently two transducers are used side-by-side and the processing means comprises a comparison circuit which is employed to look for differences between the output of one transducer, positioned where it is most sensitive to the presence of the target material, e.g. the target gas, and the output another transducer positioned where it can receive radiation from the same source but in some other part of the frequency spectrum. Monitoring for differences between the output of two transducers in this way compensates for changes in intensity of the radiation emitted from the source.

Suitably infra-red radiation is used (e.g. from a heated body, gas discharge or semiconductor source) and a prism, diffraction grating or other frequency-separating device is used to spread the radiation across a sensitive receiving area where the opto-electric transducers are positioned. One of these transducers is positioned to receive radiation at the frequency which would be absorbed by the target material or gas.

Broad band infra-red radiation can be produced by an enclosed hot filament or a suitable gas discharge and a mass-produced holographic focusing diffraction grating can be used to focus the infra-red spectrum onto the detector means (preferably a dual element pyroelectric device) which is sensitive to changes in the level of illumination falling upon it due to absorption by the target material or gas.

A concentration of 500 ppm CO is not generally fatal, whereas exposure to 1000 ppm may be fatal after 100 minutes or so. A 500 ppm concentration of CO in a path length of 20 centimeters will lead to a change in the transmitted intensity in the 4.5 to 5 micron wavelength band of approximately 0.1%. A 1 $mm^2$ hot filament operating at 1500K. produces about a milliwatt in this wavelength band in a solid angle of 0.25 steradians, the solid angle subtended by a 5 cm square diffraction grating at 10 cm from the filament source and the pyroelectric detector. A 0.1% change in intensity in the 4.5 to 5 micron wavelength band is expected to lead to a relative change in the power received by an appropriate sensor of a few microwatts and that is significantly larger than the minimum radiation power detectable by many commercially available pyroelectric detectors (which is typically of the order of $10^{-9}$ $W/Hz^{1/2}$).

BRIEF DESCRIPTION OF DRAWINGS

Embodiments of the invention will now be described, by way of example only, with particular reference to the accompanying drawings, in which.

BEST MODES FOR CARRYING OUT THE INVENTION

Figure 1:
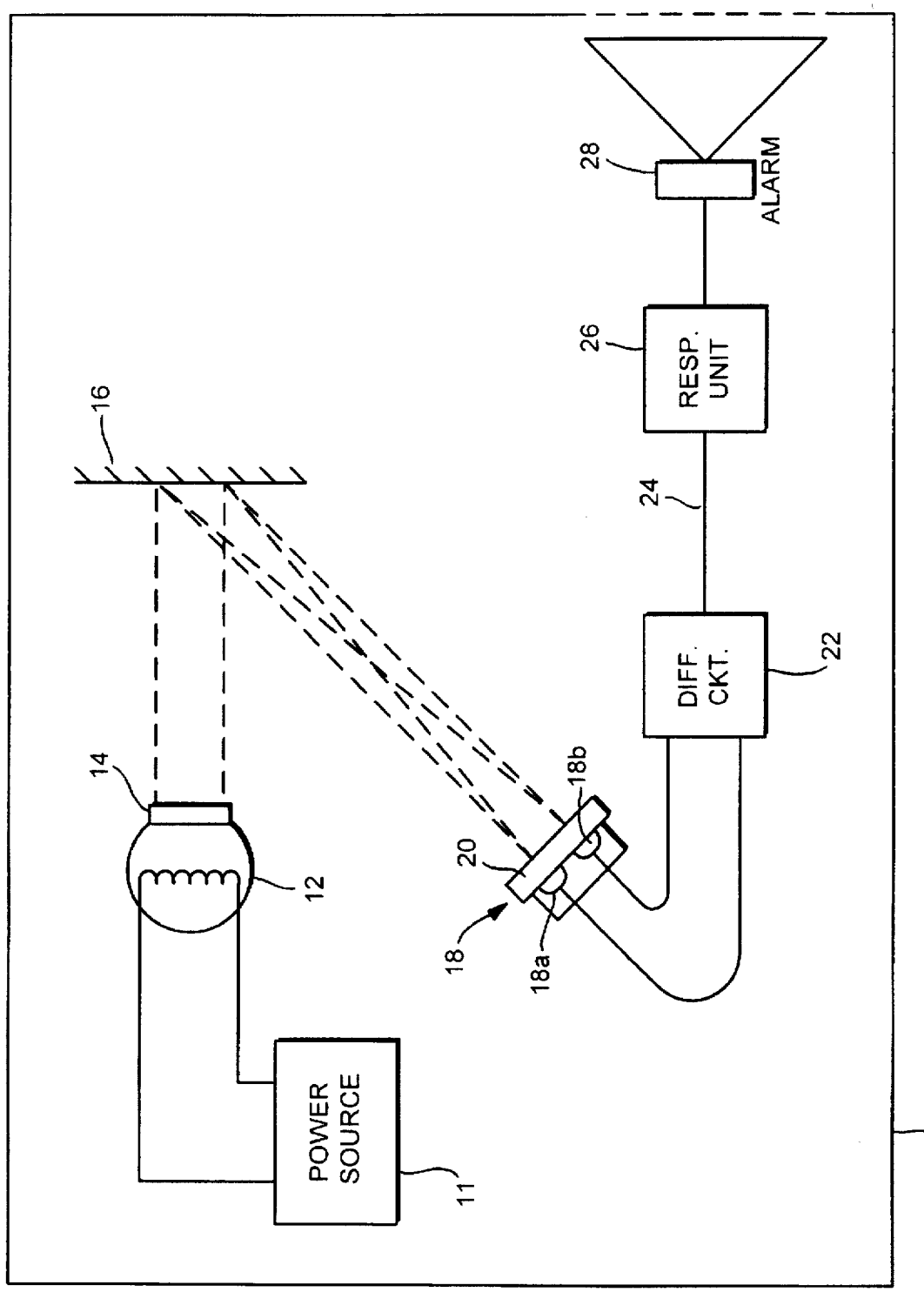
FIG. 1 is a schematic plan of detecting apparatus according to the invention.

In FIG. 1 there is shown a chamber or box 10 in which there is housed a power source 11 for an infra-red radiating bulb 12 having a window 14 (e.g. made from infra-red transmitting material such as zinc selenite, silicon or sapphire). A plastics material such as polyethylene may also be usable for the window 14.

The broad band infra-red radiation from the source 12 is directed towards dispersing or frequency-separating means in the form of a focusing holographic diffraction grating 16 which can be created on a metallic- (e.g. aluminium-) coated Mylar sheet which gives a high reflectivity. Typically the grating 16 is positioned about 10 cm from the window 14. Such gratings can be mass-produced at low cost, and can be flat and self-adhesive. A reciprocal dispersion of 1 micron per millimeter can be achieved with a grating spacing of 10 microns or so.

The infra-red spectrum from the grating 16 is focused on to a dual element pyroelectric detector 18 comprising a first detector element 18a positioned where it will receive radiation in the 4.5 to 5 micron band and a second detector element 18b positioned to receive a neighbouring band where absorption of CO does not occur. A typical spacing of the two detector elements would be around 1 millimeter in the device being described. The sort of detector elements used currently for motion detectors would be suitable and one such type is known under the trade name "Hammamatsu P2288". A window 20 of the detector 18 which is opaque to visible radiation but transparent to the radiation being monitored is positioned in front of the detector elements 18a and 18b. A thin plate of silicon can serve as the window 20.

Because the detector 18 employs two detector elements monitoring in different wavelength bands, by providing a difference circuit 22 to compare the outputs from the two detector elements it is possible to make the detector 18 insensitive to fluctuations in the level of illumination from the source 12 and also to changes in temperature, supply voltage and ambient pressure.

A second single or multi-element pyroelectric detector viewing an electromagnetic radiation path not open to the ambient atmosphere may also be used to improve sensitivity to CO or to other gases if required. Other gases could be detected in isolation by operating in a different part of the infra-red spectrum or a number of gases could be detected simultaneously using a multi-element opto-electric detector. Since the detector 18 only responds to changing "illumination", and it is not necessary to detect for CO continually, the source 12 can be pulsed on and off. An "on" pulse of only a few seconds every several minutes optimises the pyroelectric detector response and keeps the power consumption of the device low.

As an alternative to a hot filament bulb, a low-cost mass-produced flash unit (similar to a camera flash unit but with a suitable IR transmitting window) could be used as the source 12.

When the opto-electric detector 18 detects a difference in IR illumination of a few microwatts between the two transducers 18a and 18b, the circuit 22 generates an output on line 24 which actuates a response unit 26 (e.g. to power a alarm siren 28 such as a warning light).

Operation in frequency bands other than the infra-red is clearly possible if that would be suitable to the target gas in question. Furthermore, the apparatus can be used for the detection of smoke in an environment, e.g. a room or the like.

Figure 2:
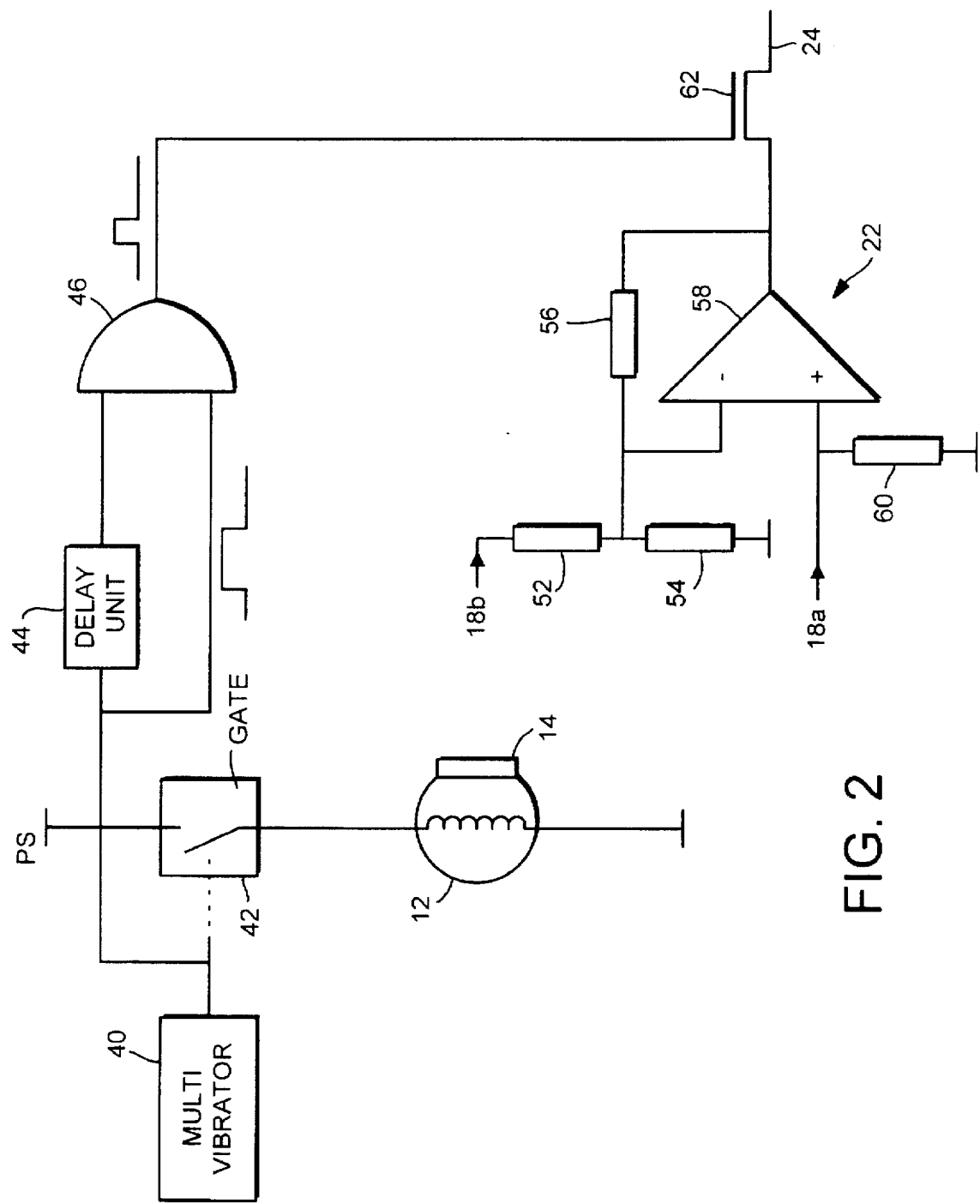
FIG. 2 shows part of the electric circuitry of the apparatus shown in FIG. 1.

A possible embodiment of the power source 11 and circuit 22 of the invention is shown in FIG. 2. The functioning of this circuit is entirely conventional and straightforward and many other possible arrangements can be envisaged. It is to be emphasized that the electronic details of 11,22,24 and 26 are ancillary to the basic invention. In FIG. 2, a free-running multivibrator 40 generates a short duty cycle that controls a gate 42 connected between the power supply PS and the source 12. The power supply, which may be voltage or current regulated, supplies all parts of the circuit. The "on" time will normally be chosen to be somewhat longer than the time required by the source 12 to reach a stable operating temperature, typically 2 secs. The "off" time has no upper limit, and will normally only be dictated by the required frequency of measurements of the air composition, typically once every 100 secs. The signals from the detectors 18a and 18b are converted into voltages, if necessary, and applied to alternative inputs of the operational amplifier 58. One of the signals is attenuated by means of the resistive divider formed by resistors 52 and 54. The values of resistors 52 and 54 are chosen such that a zero signal is obtained at the output of the amplifier 58 when no radiation-absorbing gas is present. The output from the operational amplifier 58 is supplied to a pass gate 62 before being sent to the response unit 26 via line 24. The pass gate 62 is first opened after a short period set by delay unit 44. The delay period is initiated by an on pulse issuing from the multivibrator 40. The delay time is chosen so as to allow the source 12 to reach its steady state-temperature. The gating ensures that the measurement is restricted to times when the source 12 is operating under steady state conditions.

Various refinements to the FIG. 2 circuit, such as temperature compensation, noise blanking, adjustable trimmer resistors and/or microprocessor control would clearly be advantageous in certain situations where the extra cost incurred could be tolerated.

Figure 3A:
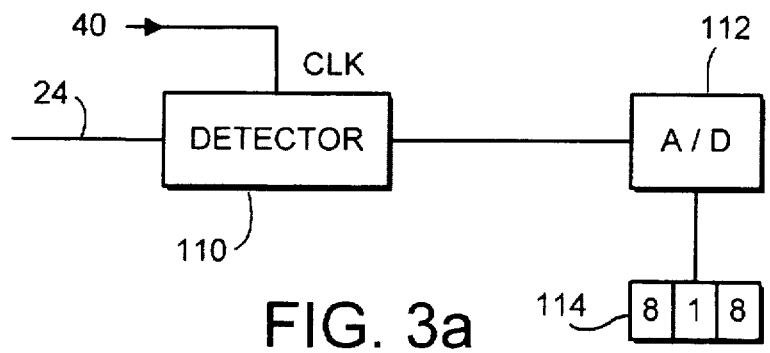
FIGS. 3a–c show different electric circuits for a response unit of the apparatus shown in FIG. 1.
Figure 3B:
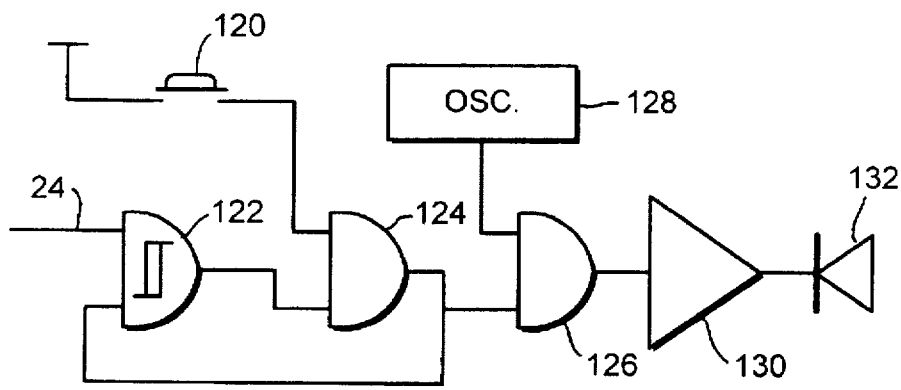
Figure 3C:
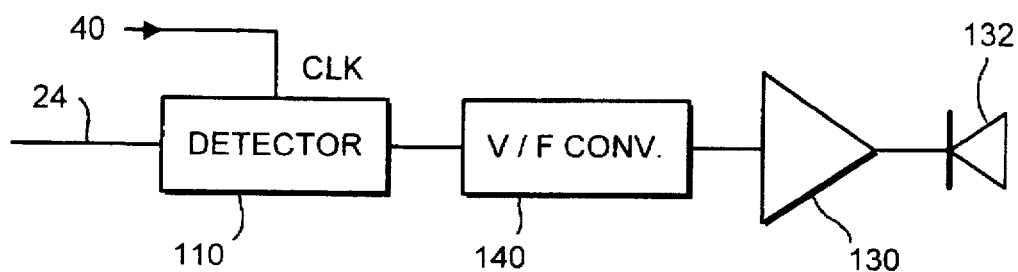

FIGS. 3a, 3b and 3c show possible embodiments of the response unit 26.

FIG. 3a shows a sample-and-hold detector 110 that is synchronized with the pulses applied to the source 12 by means of its CLK input. The detector 110 could also be a resettable peak detector. The sampled value is digitalized in an analogue-to-digital converter 112 and the output supplied to a digital display 114.

FIG. 3b shows a latch 122,124 with Schmitt trigger input gate 122 and manual reset 120. The output from a free-running (e.g. klaxon) oscillator 128 is gated by 126 and supplied to an audio amplifier 130 and acoustical transducer 132.

FIG. 3c shows a sample-and-hold detector 110 that is synchronized with the pulses applied to the source 12 by means of its CLK input, as in the response unit shown in FIG. 3a. The output from detector 110 is used to control a voltage-to-frequency converter 140, the amplified output of which is then applied to the acoustical transducer 132. In this example, the pitch of the tone changes with increasing gas concentration.

Many other embodiment of both analog and digital response unit 26 can be envisaged. For example, a radio transmitter could be incorporated so as to enable remote monitoring.

The embodiment of the basic invention shown in FIG. 1 is relatively sensitive to changes in the temperature of the radiation emitted by the source 12. This sensitivity is an artifact of the Planck radiation law:

$$\text{Radiation density, } \rho(v) \propto \frac{v^3}{e^{hv/KT} - 1}$$

according to which the ratio of energies emitted at two different wavelengths depends upon temperature. This variation with temperature is naturally undesirable in that it mimics the absorption dip that is to be detected by detector 18. The sensitivity of the gas detector according to the invention will therefore be reduced in situations where it is not possible to hold the temperature of the source 12 precisely constant. The dependence of the intensity ratio upon temperature is approximately linear for the small temperature excursions that are to be expected in a device according to the present invention, the constant of proportionality being approximately $3 \times 10^{-5}/°$ K. when T=1500° K. and the wavelength separation is 0.1 μm. One possible way of improving the performance in such situations is to provide at least one extra detector element in 18 that is positioned to observe the radiation at at least one further wavelength.

Figure 4:
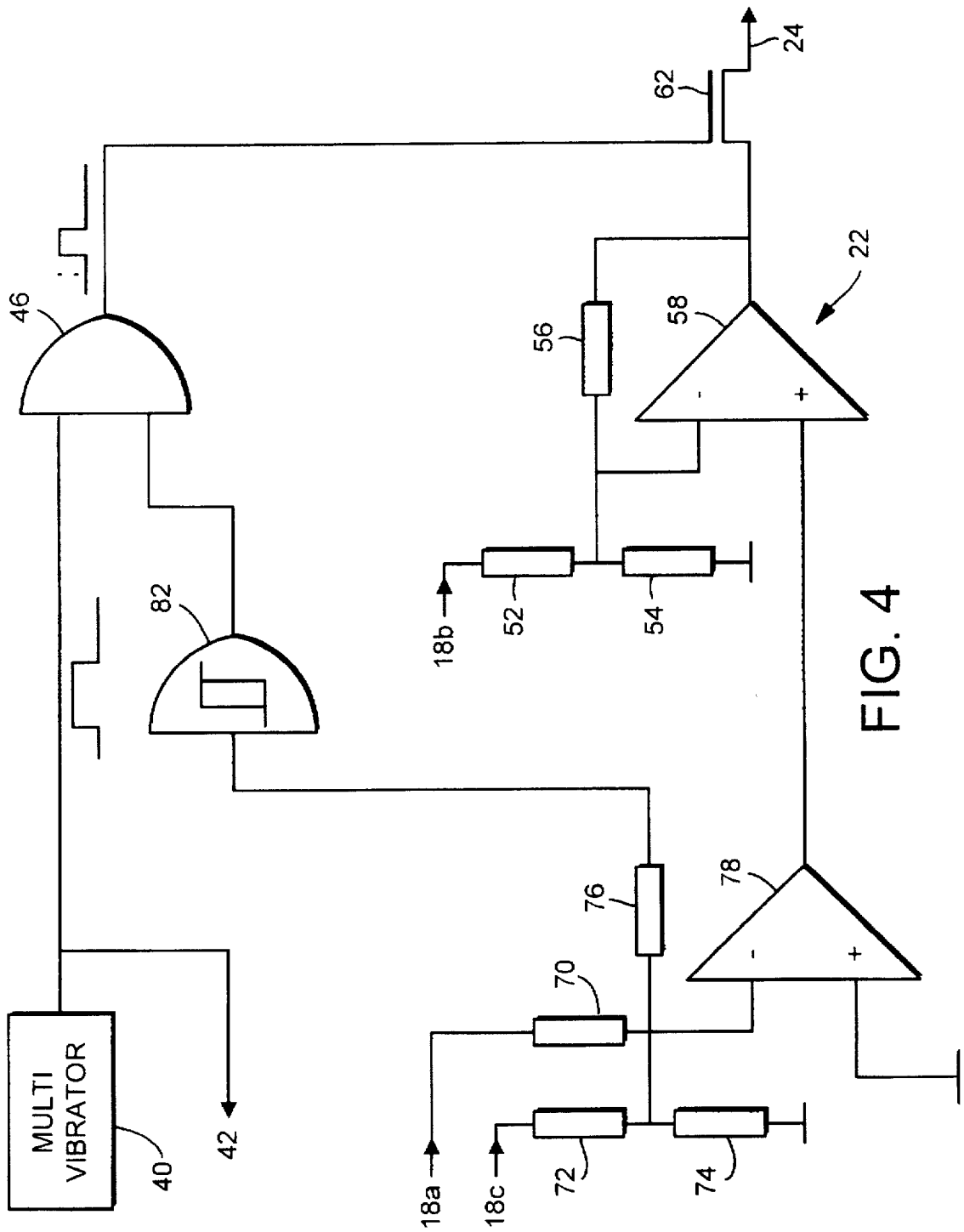
FIG. 4 shows modified electric circuitry for detecting apparatus according to the invention having three detector elements.

FIG. 4 shows one possible circuit arrangement for processing the signals from three detector elements 18. In this further embodiment of the invention, one detector 18a is positioned to receive radiation at a wavelength slightly lower than the absorption band. A second detector 18b is positioned to receive radiation at a wavelength in the centre of the absorption band, and a third detector 18c is positioned to receive radiation at a wavelength slightly higher than the absorption band. The three detector elements 18 will normally be placed equidistant to one another, but numerous other geometries will suggest themselves to the skilled practitioner. For instance, when it is desired to discriminate between two or more gases with closely spaced or partially-overlapping absorption bands, a non-symmetrical disposition of the various detectors elements may be advantageous. In each given case, the gain factors applied to the signal from each detector 18 can be chosen so as to give at least a first order cancellation of the effect of varying radiation temperature upon the detected signal as predicted by the equation for radiation density given above.

In FIG. 4, the total radiation received by the outer pair of detectors 18a and 18c is used as a measure of the absolute temperature. Once the output from 78 has reached the threshold value of the Schmitt trigger 82, AND gate 46 provides an activating voltage to the pass gate 62 for the remainder of the duration of the pulse from multivibrator 40. This gating arrangement allows one to dispense with the delay unit 44 employed in the FIG. 2 circuit.

For technical and/or economical reasons it may be advantageous to employ four or more detector elements 18 even when only one gas is to be detected. As in the circuits according to FIGS. 2 and 4, the relative amplification of each detected signal can be set by appropriate choice of the various resistors in the amplification path. The appropriate factors can in each case be routinely calculated by means of linear algebra and/or matrix methods on the basis of the radiation density equation given above and the empirically determined optical transmission co-efficients. In view of their routine nature, details of such calculations need not be provided here. Depending upon the cost and complexity of any particular implementation of the invention, the relative gain ratios could also be set by one of the following alternative well-known methods:

i) voltage dependent resistors controlled by compensated voltages ii) switched resistor arrays controlled by look-up tables stored in non-volatile memory.

While the invention has been particularly shown and described with reference to a small number of exemplary embodiments thereof, it will be understood by those skilled in the art of measurement and instrumentation technique that the foregoing and other changes in form and detail may be made without departing from the scope of the invention as defined in claim 1.

Figure 5:
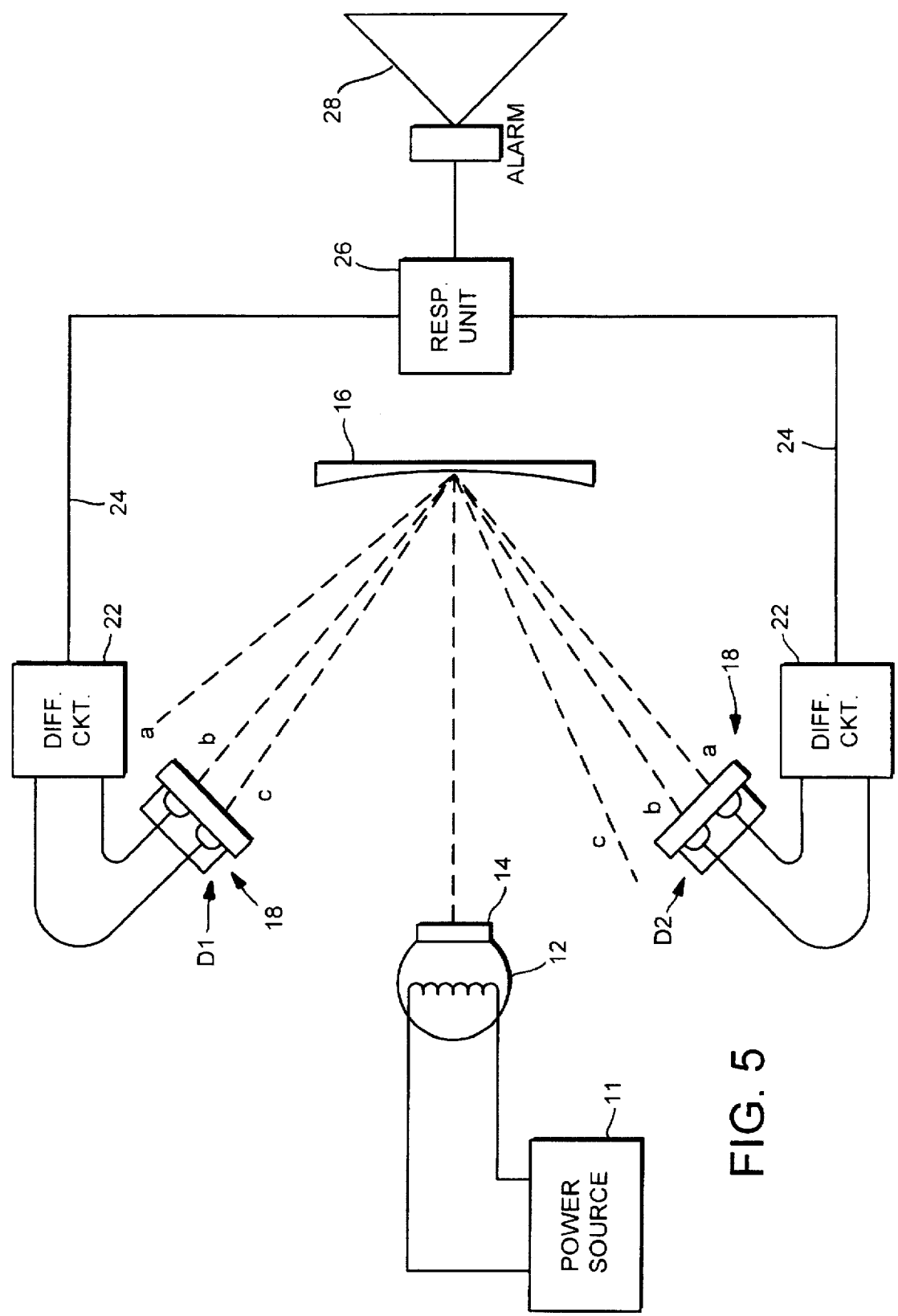
FIG. 5 is a further embodiment of detecting apparatus according to the invention employing two dual-element opto-electric detectors.

Another implementation of detecting apparatus using two dual-element opto-electric detectors is shown in FIG. 5. Detector D1 receives radiation in the absorption band for the target gas (b) and radiation at a shorter wavelength band (c). The outputs are compared to give a signal proportional to the difference between the intensities of radiation received by the two elements of the detector. Similarly a second identical detector D2 receives radiation in the absorption band (b) and radiation at a longer wavelength band (a). This could be achieved by using positive and negative diffraction orders of the diffraction grating to illuminate the two detectors 1 and 2 respectively. The difference in the signals from detector 1 and detector 2 is proportional to the absorption by the target gas and is insensitive to variations in the temperature of the source.

We claim:

1. Apparatus for detecting the presence of a target material in a fluent composition, the apparatus comprising:

a source of electromagnetic radiation;

detector means for detecting said electromagnetic radiation from said source after passage through said fluent composition, the detector means comprising at least three spaced apart opto-electric transducers for respectively detecting selected frequency bands for which the target material has different specific absorptivities, a first of said transducers being arranged to detect radiation at an absorption band of said target material, at least two other of said transducers being arranged to detect radiation at a frequency other than said absorption band;

dispersive means for presenting the electromagnetic radiation at each of said different frequency bands to a respective one of said transducers; and processing means for detecting changes in the output of said transducers occasioned by partial absorption of the electromagnetic radiation from said source by the target material and for compensating for temperature variations in said source.

2. The apparatus of claim 1, wherein one of said at least two other transducers is arranged to detect radiation at a frequency above said absorption band and another of said at least two other transducers is arranged to detect radiation at a frequency below said absorption band.

3. The apparatus of claim 1, wherein the processing means is adapted to compare changes in the outputs of said opto-electric transducers to enable detection of the presence or otherwise of said target material.

4. The apparatus of claim 1, wherein the transducers are pyroelectric transducers.

5. The apparatus of claim 1, wherein the detector means comprises two dual-element detectors.

6. The apparatus of claim 1, wherein the dispersive means comprises a diffraction grating.

7. The apparatus of claim 1, wherein the dispersive means comprises a prism.

8. The apparatus of claim 1, wherein said source comprises a hot filament device.

9. The apparatus of claim 1, wherein the transducers are equidistant from one another.

10. A method for detecting the presence of a target material in a fluent composition, the method comprising the steps of:

dispersing electromagnetic radiation emitted from a source into bands of different frequencies for which the target material has different specific absorptivities;

detecting in detector means the dispersed electromagnetic radiation emitted after it has been passed through said fluent composition, the different frequency bands being detected by at least three spaced apart opto-electric transducers comprising said detector means, a first of said transducers detecting radiation at an absorption band of said target material, at least two other of said transducers detecting radiation at a frequency other than said absorption band; and processing the outputs of said transducers occasioned by partial absorption of the electromagnetic radiation from said source by the target material to indicate the presence of said target material and for compensating for temperature variations in said source.

11. The method of claim 10, wherein one of said at least two other transducers detects radiation at a frequency above said absorption band and another of said at least two other transducers detects radiation at a frequency below said absorption band.

12. A method according to claim 10, wherein a warning signal is derived on a comparison of the outputs of said opto-electric transducers.

13. A method according to claim 10, wherein the emitted electromagnetic radiation comprises broadband infrared radiation.

14. A method for detecting the presence of a target material in a fluent composition, the method comprising the steps of:

emitting electromagnetic radiation from a source into bands of different frequencies for which the target material has different specific absorptivities for partial absorption thereof;

dispersing electromagnetic radiation through the fluent material;

detecting the different frequency bands of the dispersed electromagnetic radiation emitted after it has been passed through said fluent composition, the different frequency bands being detected by at least three spaced apart opto-electric transducers, a first of said transducers responsive to radiation at an absorption band of said target material, and the two other of said transducers detecting radiation at a frequency other than said absorption band; and processing the outputs of said transducers occasioned by partial absorption of the electromagnetic radiation by the target material in the fluent material to indicate the presence of said target material therein and for compensating for temperature variations in said source.

* * * * *